(12) United States Patent
Walling et al.

(10) Patent No.: US 6,455,055 B1
(45) Date of Patent: Sep. 24, 2002

(54) COSMETIC COMPOSITIONS

(75) Inventors: David William Walling, Cincinnati; Michael Lee Vatter, Okeana, both of OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/467,937

(22) Filed: Dec. 21, 1999

Related U.S. Application Data

(63) Continuation-in-part of application No. 09/249,939, filed on Feb. 12, 1999, now abandoned.

(51) Int. Cl.$^7$ ................................................. A61K 7/00
(52) U.S. Cl. .................... 424/401; 424/489; 424/63; 424/64; 514/355; 514/844; 514/847; 514/951
(58) Field of Search ........................... 424/401, 489, 424/63, 64; 514/355, 844, 847, 951

(56) References Cited

U.S. PATENT DOCUMENTS

| | | | |
|---|---|---|---|
| 4,082,846 A | 4/1978 | Clark | 424/266 |
| 4,096,240 A | 6/1978 | Mathur | 424/59 |
| 4,699,924 A | 10/1987 | Durrant et al. | 514/558 |
| 4,758,599 A | 7/1988 | Minetti | 514/844 |
| 4,777,034 A | 10/1988 | Olivier et al. | 424/65 |
| 4,873,085 A | 10/1989 | Fuisz | 424/400 |
| 4,940,666 A | 7/1990 | Boyce et al. | 435/240.2 |
| 4,944,937 A | 7/1990 | McCall | 424/65 |
| 5,085,856 A | 2/1992 | Dunphy et al. | 424/64 |
| 5,254,331 A | 10/1993 | Mausner | 424/59 |
| 5,310,547 A | 5/1994 | Dunphy et al. | 424/64 |
| 5,425,939 A | 6/1995 | Guerrero et al. | 424/78.02 |
| 5,429,816 A | 7/1995 | Hofrichter et al. | 424/66 |
| 5,449,512 A | 9/1995 | Simmons | 424/73 |
| 5,472,687 A | 12/1995 | Proctor | 424/70.1 |
| 5,496,827 A | 3/1996 | Patrick | 514/310 |
| 5,527,350 A | 6/1996 | Grove et al. | 607/89 |
| 5,571,794 A | 11/1996 | Frome | 514/23 |
| 5,582,817 A | 12/1996 | Otsu et al. | 424/59 |
| 5,593,662 A | 1/1997 | Deckner et al. | 424/64 |
| 5,658,576 A | 8/1997 | Soudant | 424/401 |
| 5,665,339 A | 9/1997 | Simmons | 424/73 |
| 5,688,831 A | 11/1997 | El-Nokaly et al. | 514/938 |
| 5,744,149 A | 4/1998 | Girardot | 424/402 |
| 5,804,594 A | 9/1998 | Murad | 514/474 |
| 5,833,998 A | 11/1998 | Biedermann et al. | 424/401 |
| 5,843,407 A | 12/1998 | El-Nokaly et al. | 424/64 |
| 5,853,712 A | 12/1998 | Langlois | 424/78.03 |
| 6,024,976 A | 2/2000 | Miranda et al. | 424/449 |

FOREIGN PATENT DOCUMENTS

| | | |
|---|---|---|
| DE | 4328871 A1 | 3/1995 |
| EP | 0 512 814 A1 | 11/1992 |
| EP | 0 522 618 A1 | 1/1993 |
| EP | 0 522 624 A1 | 1/1993 |
| EP | 0 524 892 B1 | 1/1993 |
| EP | 0 748 622 A1 | 12/1996 |
| EP | 0 852 946 A2 | 7/1998 |
| FR | 3203 M | 3/1965 |
| FR | 2513879 | 4/1983 |
| FR | 2694692 | 2/1994 |
| JP | 61-063615 | 4/1986 |
| JP | 61-083110 | 4/1986 |
| JP | 04-305512 | 10/1992 |
| JP | 06-087730 A | 3/1994 |
| JP | 06-107531 | 4/1994 |
| JP | 09-002952 | 1/1997 |
| JP | 10-139676 | 5/1998 |
| JP | 10-194954 | 7/1998 |
| JP | 10-194958 | 7/1998 |
| JP | 11-269054 | 10/1999 |
| WO | 94/06400 A1 | 3/1994 |
| WO | 96/07396 A2 | 3/1996 |
| WO | 97/01345 A1 | 1/1997 |
| WO | 97/01346 A1 | 1/1997 |
| WO | 97/31620 A2 | 9/1997 |
| WO | 98/33475 A1 | 8/1998 |
| WO | 98/52530 | 11/1998 |
| WO | 9852927 | * 11/1998 |
| WO | 98/52929 A1 | 11/1998 |

OTHER PUBLICATIONS

"Niacinamide 99% "Degussa" Feed Grade," Jan. 27, 1998.
Saturday Morning Subspecialty Session: "Stimulation of Collagen Type I and Type III mRNA Synthesis in Human Skin Fibroblasts by Ninotinamide." BK Tay, MZ Hussain, TK Hunt (intro by LH Smith). Dept. of Stomatology and Dept. of Surgery, University of California, San Francisco, Feb. 9, 1991.

* cited by examiner

*Primary Examiner*—Michael A. Williamson
(74) *Attorney, Agent, or Firm*—Armina E. Matthews; Tara M. Rosnell; Steven W. Miller

(57) ABSTRACT

Disclosed are cosmetic compositions including lipsticks, comprising from about 0.01% to about 50%, by weight, of a crystalline vitamin $B_3$ compound having an average particle size of from about 0.01 μm to about 200 μm; from about 1% to about 90%, by weight, of an emollient component; and from about 1% to about 90%, by weight, of a solidifying agent. The compositions provide improved skin feel of crystalline vitamin $B_3$ compounds when applied to skin.

24 Claims, No Drawings

COSMETIC COMPOSITIONS

CROSS REFERENCE TO RELATED APPLICATION

This application is a continuation-in-part of prior application Ser. No. 09/249,939 filed on Feb. 12, 1999 now abandoned.

FIELD OF THE INVENTION

The present invention relates to topical cosmetic compositions containing crystalline vitamin $B_3$ compounds dispersed in an emollient or oil phase.

BACKGROUND OF THE INVENTION

Niacin, also known as vitamin $B_3$, is the common name for nicotinic acid. The physiologically active form of niacin is niacinamide, also a member of the vitamin $B_3$ family of compounds. Niacin and niacinamide (nicotinic acid amide) function in the body as components of two coenzymes: nicotinamide adenine dinucleotide (NAD) and nicotinamide adenine dinucleotide phosphate (NADP). Until recently, these vitamin $B_3$ compounds were used exclusively to treat niacin deficiency and pellegra.

Today, however, solubilized vitamin $B_3$ compounds have also found use in the area of skin care actives. British Patent 1,370,236 describes compositions for skin lightening containing 0.5% to 10% niacin. Similarly, U.S. Pat. No. 4,096,240 discloses the use of 0.1% to 10% niacinamide for skin lightening. Vitamin $B_3$ compounds have also been found useful in regulating the texture of human skin. See PCT application WO 97/39733, to Oblong et al.

However, when applied to the skin in crystalline form (i.e., powder), vitamin $B_3$ compounds tend to impart a rough feel to the skin. In the past, the crystalline vitamin $B_3$ compounds were solubilized in a polar solvent before application to skin, thus alleviating the rough feel of the crystals. However, solubilization reduced the efficacy of the vitamin $B_3$ compound upon contact with the skin. Thus there exists a need for cosmetic compositions comprising unsolubilized crystalline vitamin $B_3$ compound(s) which provide improved consumer perceived skin feel. The present inventors have discovered that cosmetic formulations incorporating the crystalline vitamin $B_3$ compounds of specific particle size in combination with an emollient, improve the consumer perceived feel of the crystalline vitamin $B_3$ compound on the skin. The present inventors have further discovered that these compositions are especially useful to impart vitamin $B_3$ benefits to the lips with improved skin feel when used in lipstick compositions including a solidifying agent.

It is, therefore, an aspect of the present invention to provide cosmetic compositions, preferably anhydrous cosmetic compositions, comprising crystalline vitamin $B_3$ compounds which improve the appearance and feel of the skin while alleviating the rough feel of the crystalline vitamin $B_3$ compound.

Another aspect of the present invention is to provide cosmetic compositions comprising crystalline vitamin $B_3$ compounds having reduced particle size.

A further aspect of the present invention is to provide substantially anhydrous lip compositions such as lipsticks and lip-paints, comprising crystalline vitamin $B_3$ compounds having reduced particle size.

These and other aspects will become readily apparent from the detailed description which follows.

SUMMARY OF THE INVENTION

The present invention relates to cosmetic compositions providing improved skin feel, which contain from about 0.01% to about 50%, by weight, of a crystalline vitamin $B_3$ compound having an average particle size of from about 0.01 μm to about 200 μm; from about 1% to about 90%, by weight, of an emollient component; and from about 1% to about 90%, by weight, of a solidifying agent. The compositions of the present invention are useful for improving consumer perceived skin feel of crystalline vitamin $B_3$ compounds when applied to the skin.

All percentages, parts and ratios are based upon the total weight of the cosmetic compositions of the present invention, unless otherwise specified. All such weights as they pertain to listed ingredients are based on the active level and, therefore, do not include carriers or by-products that may be included in commercially available materials, unless otherwise specified.

DETAILED DESCRIPTION OF THE INVENTION

As used herein, the term "cosmetics" includes make-up, foundation, and skin care products. The term "make-up" refers to products that leave color on the face, including foundation, blacks and browns, i.e., mascara, concealers, eye liners, brow colors, eye shadows, blushers, lip colors, and so forth. Skin care products are those used to treat or care for, or somehow moisturize, improve, or clean the skin. Products contemplated by the phrase "skin care products" include, but are not limited to, adhesives, bandages, toothpaste, anhydrous occlusive moisturizers, antiperspirants, deodorants, powder laundry detergent, fabric softener towels, occlusive drug delivery patches, nail polish, powders, tissues, wipes, solid emulsion compact, hair conditioners-anhydrous and the like. The term "foundation" refers to liquid, creme, mousse, pancake, compact, concealer or like product created or reintroduced by cosmetic companies to even out the overall coloring of the skin. Foundation is manufactured to work better over moisturized and/or oiled skin.

As used herein the term "comprising" means that the composition can contain other ingredients which are compatible with the composition and which preferably do not substantially disrupt the compositions of the present invention. The term encompasses the terms "consisting of" and "consisting essentially of".

Essential Components

Vitamin $B_3$ Compound

The compositions of the present invention comprise a safe and effective amount of a natural or synthetic vitamin $B_3$ compound in crystalline form. The compositions of the present invention preferably comprise from above 0.01% to about 50%, more preferably from about 0.1% to about 30%, even more preferably 0.5% to about 20%, most preferably from about 1% to about 10% of the vitamin $B_3$ compound.

As used herein, "vitamin $B_3$ compound" means a compound having the formula:

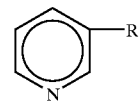

wherein R is—$CONH_2$ (i.e., niacinamide),—COOH (i.e., nicotinic acid) or—$CH_2OH$ (i.e., nicotinyl alcohol); derivatives of niacinamide, nicotinic acid, and/or nicotinyl alcohol; and salts of any of the foregoing.

Exemplary derivatives of the foregoing vitamin $B_3$ compounds include nicotinic acid esters, including non-vasodilating esters of nicotinic acid, nicotinyl amino acids, and nicotinyl alcohol esters of carboxylic acids.

Suitable esters of nicotinic acid include nicotinic acid esters of $C_1$–$C_{22}$, preferably $C_1$–$C_{16}$, more preferably $C_1$–$C_6$ alcohols. The alcohols are suitably straight-chain or branched chain, cyclic or acyclic, saturated or unsaturated (including aromatic), and substituted or unsubstituted. The esters are preferably non-rubifacient. As used herein, "non-rubifacient" means that the ester does not commonly yield a visible flushing response after application to the skin in the subject compositions (the majority of the general population would not experience a visible flushing response, although such compounds may cause vasodilation not visible to the naked eye). Alternatively, a nicotinic acid material which is rubifacient at higher doses could be used at a lower dose to reduce the rubifacient effect. Non-rubifacient esters of nicotinic acid include tocopherol nicotinate and inositol hexanicotinate; tocopherol nicotinate is preferred.

Other derivatives of the vitamin $B_3$ compound are derivatives of niacinamide resulting from substitution of one or more of the amide group hydrogens. Nonlimiting examples of derivatives of niacinamide useful herein include nicotinyl amino acids, derived, for example, from the reaction of an activated nicotinic acid compound (e.g., nicotinic acid azide or nicotinyl chloride) with an amino acid, and nicotinyl alcohol esters of organic carboxylic acids (e.g., C1–C18). Specific examples of such derivatives include nicotinuric acid and nicotinyl hydroxamic acid, which have the following chemical structures:

nicotinuric acid:

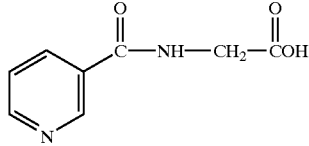

nicotinyl hydroxamic acid:

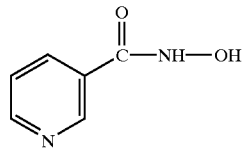

Exemplary nicotinyl alcohol esters include nicotinyl alcohol esters of the carboxylic acids salicylic acid, acetic acid, glycolic acid, palmitic acid and the like. Other non-limiting examples of vitamin $B_3$ compounds useful herein are 2-chloronicotinamide, 6-aminonicotinamide, 6-methylnicotinamide, n-methyl-nicotinamide, n,n-diethylnicotinamide, n-(hydroxymethyl)nicotinamide, quinolinic acid imide, nicotinanilide, n-benzylnicotinamide, n-ethylnicotinamide, nifenazone, nicotinaldehyde, isonicotinic acid, methyl isonicotinic acid, thionicotinamide, nialamide, 1-(3-pyridylmethyl) urea, 2-mercaptonicotinic acid, nicomol, and niaprazine.

Examples of the above vitamin $B_3$ compounds are well known in the art and are commercially available from a number of sources, e.g., the Sigma Chemical Company (St. Louis, Mo.); ICN Biomedicals, Inc. (Irvin, Calif.) and Aldrich Chemical Company (Milwaukee, Wis.).

One or more vitamin $B_3$ compounds may be used herein. Preferred vitamin $B_3$ compounds are niacinamide and tocopherol nicotinate. Niacinamide is more preferred.

Salts of the vitamin $B_3$ compound are also useful herein. Nonlimiting examples of salts of the vitamin $B_3$ compound useful herein include organic or inorganic salts, such as inorganic salts with anionic inorganic species (e.g., chloride, bromide, iodide, carbonate, preferably chloride), and organic carboxylic acid salts (including mono-, di- and tri-C1–C18 carboxylic acid salts, e.g., acetate, salicylate, glycolate, lactate, malate, citrate, preferably monocarboxylic acid salts such as acetate). These and other salts of the vitamin $B_3$ compound can be readily prepared by the skilled artisan, for example, as described by W. Wenner, "The Reaction of L-Ascorbic and D-Isoascorbic Acid with Nicotinic Acid and Its Amide", J. Organic Chemistry, VOL. 14, 22–26 (1949), which is incorporated herein by reference. Wenner describes the synthesis of the ascorbic acid salt of niacinamide.

When used, salts, derivatives, and salt derivatives of niacinamide are preferably those having substantially the same efficacy as niacinamide in the methods of regulating skin condition described herein.

In a preferred embodiment, the vitamin $B_3$ compound contains a limited amount of the salt form and is more preferably substantially free of salts of a vitamin $B_3$ compound. As used herein, "substantially free of salts" means that by weight, less than 50% of the vitamin $B_3$ compounds in the composition are in salt form. Preferably the vitamin $B_3$ compound contains less than about 20% of such salt, and is more preferably essentially free of the salt form.

In a preferred embodiment, the ring nitrogen of the vitamin $B_3$ compound is substantially chemically free (e.g., unbound and/or unhindered), or after delivery to the skin becomes substantially chemically free ("chemically free" is hereinafter alternatively referred to as "uncomplexed". More preferably, the vitamin $B_3$ compound is essentially uncomplexed. Therefore, if the composition contains the vitamin $B_3$ compound in a salt or otherwise complexed form, such complex is preferably substantially reversible, more preferably essentially reversible, upon delivery of the composition to the skin. For example, such complex should be substantially reversible at a pH of from about 5.0 to about 6.0. Such reversibility can be readily determined by one having ordinary skill in the art.

More preferably the vitamin $B_3$ compound is substantially uncomplexed in the composition prior to delivery to the skin. Exemplary approaches to minimizing or preventing the formation of undesirable complexes include omission of materials which form substantially irreversible or other complexes with the vitamin $B_3$ compound, pH adjustment, ionic strength adjustment, the use of surfactants, and formulating wherein the vitamin $B_3$ compound and materials which complex therewith are in different phases. Such approaches are well within the level of ordinary skill in the art.

The vitamin $B_3$ compound may be included as the substantially pure material, or as an extract obtained by suitable physical and/or chemical isolation from natural (e.g., plant) sources. The vitamin $B_3$ compound is preferably substantially pure, more preferably essentially pure.

The vitamin $B_3$ compounds of the present invention have an average particle size of from about 0.01 $\mu$m (microns) to about 200 $\mu$m, preferably from about 0.01 $\mu$m to about 100 $\mu$m, more preferably from about 0.01 $\mu$m to about 50 $\mu$m, most preferably from about 0.01 $\mu$m to about 20 $\mu$m. Preferably, the vitamin $B_3$ compounds have a particle size distribution such that at least about 60% of the vitamin $B_3$ particles are less than about 30 $\mu$m, more preferably at least about 75% of the vitamin $B_3$ particles are less than about 30

μm, most preferably at least about 85% of the vitamin $B_3$ particles are less than about 30 μm, still more preferably at least about 90% of the vitamin $B_3$ particles are less than about 30 μm.

Emollient

The compositions of the present invention further comprise an emollient suitable for suspending or otherwise dispersing the crystalline vitamin $B_3$ compound therein. Any emollient that is known or otherwise suitable for use in cosmetic applications, and which is also compatible with the crystalline vitamin $B_3$ compound in the composition, may be used in the composition of the present invention.

Preferred emollients for use in the composition of the present invention are those materials referred to in the personal care arts as fats, oils, fatty alcohols, fatty acids, esters of fatty acids, and combinations thereof, and which aid application and adhesion, yield gloss and/or provide occlusive moisturization.

The emollient comprises from about 1% to about 90%, preferably from about 10% to about 80%, more preferably from about 20% to about 70%, and most preferably from about 40% to about 60%, of the cosmetic composition.

Suitable emollients for use in the present invention include isostearic acid derivatives, isopropyl palmitate, lanolin oil, diisopropyl dimerate, maleated soybean oil, octyl palmitate, isopropyl isostearate, cetyl lactate, cetyl ricinoleate, tocopheryl acetate, acetylated lanolin alcohol, cetyl acetate, phenyl trimethicone, glyceryl oleate, tocopheryl linoleate, wheat germ glycerides, arachidyl propionate, myristyl lactate, decyl oleate, propylene glycol ricinoleate, isopropyl lanolate, pentaerythrityl tetrastearate, neopentylglycol dicaprylate/dicaprate, hydrogenated cocoglycerides, isononyl isononanoate, isotridecyl isononanoate, myristal myristate, triisocetyl citrate, cetyl alcohol, octyl dodecanol, oleyl alcohol, panthenol, lanolin alcohol, linoleic acid, linolenic acid, sucrose esters of fatty acids, octyl hydroxystearate and mixtures thereof. Examples of other suitable emollients described in the Cosmetic Bench Reference, pp. 1.19–1.22 (1996), which descriptions are incorporated herein by reference.

Particularly preferred for use herein are non-polar emollients. By "non-polar emollient," as used herein, means any emollient emulsifier possessing no permanent electric moments and wherein the solubility (at 30° C.) of the vitamin $B_3$ compound in the polar emollient is less than about 1.5% preferably less than about 1.0%, more preferably less than about 0.5%. Suitable non-polar emollients include, but are not limited to, esters and linear or branched chained hydrocarbons, examples of which include isononyl isononanoate, isopropyl isostearate, octyl hydroxystearate, diisopropyl dimerate, lanolin oil, octyl palmitate, isopropyl palmitate, pariffins, isoparrifins, acetylated lanolin, sucrose fatty acid esters, isopropyl myristate, isopropyl stearate, mineral oil, silicone oils, dimethicone, allantoin, isohexadecane, isododecane, petrolatum, and mixtures thereof. As used herein, the solubility of the vitamin $B_3$ compound in non-polar emollients is determined by the methodology described hereinafter.

Suitable oil emollients for use in the compositions of the present invention include esters, triglycerides, hydrocarbons and silicones. These can be a single material or a mixture of one or more materials. They will normally comprise from about 1% to about 100%, preferably from about 5% to about 90%, and most preferably from about 70% to about 90% of the emollient component.

Oils can act as emollients and can also impart viscosity, tackiness, and drag properties to cosmetic compositions such as lipsticks. Examples of suitable oils include caprylic triglycerides; capric triglyceride; isostearic triglyceride; adipic triglyceride; propylene glycol myristyl acetate; lanolin; lanolin oil; polybutene; isopropyl palmitate; isopropyl myristate; isopropyl isostearate; diethyl sebacate; diisopropyl adipate; tocopheryl acetate; tocopheryl linoleate; hexadecyl stearate; ethyl lactate; cetyl oleate; cetyl ricinoleate; oleyl alcohol; hexadecyl alcohol; octyl hydroxystearate; octyl dodecanol; wheat germ oil; hydrogenated vegetable oils; castor oil; petrolatum; modified lanolins; branched-chain hydrocarbons; alcohols and esters; corn oil; cottonseed oil; olive oil; palm kernel oil; rapeseed oil; safflower oil; jojoba oil; evening primrose oil; avocado oil mineral oil, sheabutter, octylpalmitate, maleated soybean oil, glycerol trioctanoate, diisopropyl dimerate, and volatile and non-volatile silicone oils including phenyl trimethicone.

The preferred oils for use herein are acetylglycerides, octanoates, and decanoates of alcohols and polyalcohols, such as those of glycol and glycerol, the ricinoleates of alcohols and polyalcohols such as cetyl ricinoleate, PG-3 diisostearate, polyglycerol ethers, polyglycerol esters, caprylic triglycerides, capric triglycerides, isostearic triglyceride, adipic triglyceride, phenyl trimethicone, lanolin oil, polybutene, isopropyl palmitate, isopropyl isostearate, cetyl ricinoleate, octyl dodecanol, oleyl alcohol, hydrogenated vegetable oils, castor oil, modified lanolins, octyl palmitate, lanolin oil, maleated soybean oil, cetyl ricinoleate, glyceryl trioctanoate, diisopropyl dimerate, synthetic lanolin derivatives and branched chain alcohols, sucrose esters of fatty acids, octyl hydroxystearate and mixtures thereof.

Preferably, the oils used are selected such that the majority (at least about 75%, preferably at least about 80% and most preferably at least about 99%) of the types of oils used have solubility parameters which do not differ by more than from about 1 to about 0.1, preferably from about 0.8 to about 0.1.

Optional Components

Solidifying Agent

The cosmetic compositions of the present invention may further comprise a solidifying agent to solidify or trap any liquid base materials in the cosmetic composition. As used herein, the term "solidify" refers to the physical and/or chemical alteration of the liquid base material so as to form a solid or semi-solid at ambient conditions, i.e., to form a final composition which has a stable physical structure and is deposited on the skin during normal use conditions. As is appreciated by those skilled in the art, the selection of the particular solidifying agent for use in the cosmetic compositions will depend upon the particular type of composition desired, i.e., gel or wax-based, the desired rheology, the liquid base material used and the other materials to be used in the composition. The solidifying agent is preferably present at a concentration of from about 1 to about 90%, more preferably from about 1 to about 50%, even more preferably from about 5% to about 40%, most preferably from about 3% to about 20%.

The wax cosmetic stick embodiments of this invention preferably contain from about 5% to about 50% (by weight) of a waxy solidifying agent. The term "waxy solidifying agent," as used herein, refers to a solidifying material having wax-like characteristics. Such waxy materials may also serve as emollients. Among the waxy materials useful herein are the high melting point waxes, i.e., having a melting point of from about 65° C. to about 125° C., such as beeswax, spermaceti, carnauba, baysberry, candelilla, montan, ozokerite, ceresin, paraffin, synthetic waxes such as Fisher- Tropsch waxes, microcrystalline wax, and mixtures thereof. Ceresin, ozokerite, white beeswax, synthetic waxes, and mixtures thereof, are among the preferred high-melting point waxes useful herein. Compositions containing waxes among those useful herein are disclosed in U.S. Pat. No. 4,049,792, Elsnau, issued Sep. 20, 1977, herein incorporated by reference in its entirety). Low melting waxes, having a melting point of from about 37° C. to about 75° C., are preferred for use in the wax stick embodiments of this invention. Wax stick embodiments of this invention, which contain volatile silicone oils as a liquid base material, preferably contain from about 10% to about 35%, more preferably from about 10% to about 20% (by weight), of a low-melting wax. Such materials include fatty acids, fatty alcohols, fatty acid esters and fatty acids amides, having fatty chains of from about 8 to about 30 carbon atoms, and mixtures thereof. Preferred wax-like materials include cetyl alcohol, palmitic acid, stearyl alcohol, behenamide, sucrose esters of tallow fatty acids, mono and di-fatty acid esters of polyethylene glycol, and mixtures thereof. Stearyl alcohol, cetyl alcohol, and mixtures thereof, are particularly preferred. Fatty acids, fatty alcohols, and other wax-like materials useful in this invention are also disclosed in the following references, all of which are incorporated by reference herein: U.S. Pat. No. 4,151,272, Geary, et al., issued Apr. 24, 1979; U.S. Pat. No. 4,229,432, Geria, issued Oct. 21, 1980; and U.S. Pat. No. 4,280,994, Turney, issued Jul. 28, 1981; "The Chemistry and Technology of Waxes", A. H. Warth, 2nd Edition, reprinted in 1960, Reinhold Publishing Corporation, pp 391–393 and 421; "The Petroleum Chemicals Industry", R. F. Goldstein and A. L. Waddeam, 3rd Edition (1967), E & F. N. Span Ltd., pp 33–40; "The Chemistry and Manufacture of Cosmetics", M. G. DeNavarre, 2nd edition ( 1970), Van Nostrand & Company, pp 354–376; and in "Encyclopedia of Chemical Technology:, Vol. 24, Kirk-Othmer, 3rd Edition (1979) pp 466–481. Preferred wax-like materials useful as solidifying agents in the present wax sticks are described in U.S. Pat. No. 4,126,679, Davy, et al., issued Nov. 21, 1978, herein incorporated by reference in its entirety. Preferred mixtures of wax-like materials comprise fatty alcohols containing carbon chains of from about 14 to about 18 carbon atoms, and alcohols having chain lengths of 20 carbons or longer, wherein the final mixture contains from about 1% to about 3% (by weight) of the longer-chain fatty alcohols. Compositions containing these fatty alcohol mixtures are described in European Patent Specification No. 117,070, May, published Aug.29, 1984 (incorporated by reference herein).

Also useful herein are biopolymers such as those described in European Application No. 522624, to Dunphy et al., herein incorporated by reference in its entirety.

The gel stick embodiments of this invention preferably contain from about 3% to about 30%, preferably from about 3% to about 10% (by weight), of a solidifying agent. The particular amount of solidifying agent to be used will depend upon the particular solidifying agent and the liquid base material used, and the desired physical characteristics of the gel stick. Solidifying agents useful in the gel stick embodiments of this invention are, in general, surface-active compounds which form networks immobilizing or solidifying the liquid base materials into a gel. Such solidifying agents include: soaps, such as the sodium and potassium salts of higher fatty acids, i.e., acids having from 12 to 22 carbon atoms; amides of higher fatty acids; higher fatty acid amides of alkylolamines; dibenzaldehyde-monosorbitol acetals; alkali metal and alkaline earth metal salts of the acetates, propionates and lactates; waxes, such as candelilla and carnauba waxes; and mixtures thereof. Among those solidifying agents preferred for use in the gel stick embodiments of this invention are sodium stearate, sodium palmitate, aluminum stearate, aluminum magnesium hydroxy stearate, and mixtures thereof. Gel stick compositions containing solidifying agents among those useful herein are described in the following patent documents, all incorporated herein by reference in their entirety: U.S. Pat. No. 2,900,306, Slater, issued Aug. 18, 1959; U.S. Pat. No. 3,255,082, Barton, issued Jun. 7, 1966; U.S. Pat. No. 4,137,306, Rubino, et al., issued Jan. 30, 1979; U.S. Pat. No. 4,154,816, Roehl, et al., issued May 15, 1979; U.S. Pat. No. 4,226,889, Yuhas, issued Oct. 7, 1980; U.S. Pat. No. 4,346,079, Roehl, issued Aug. 24, 1982; U.S. Pat. No. 4,383,988, Teng, et al., issued May 17, 1983; European Patent Specification No. 107,330, Luebbe, et al, published May 2, 1984; and U.S. patent application Ser. No. 630,790, DiPietro, filed Jul. 13, 1984. Preferred solidifying agents useful in the gel stick embodiments of the present invention are described in European Patent Specification No. 24,365 Sampson, et al., published Mar. 4, 1981, incorporated herein by reference in its entirety.

Also useful herein as solidifying agents are conventional thickening agents. Examples of suitable thickeners include, but are not limited to, naturally-occurring polymeric materials such as, locust bean gum, sodium alginate, sodium caseinate, egg albumin, gelatin agar, carrageenin gum sodium alginate, xanthan gum, quince seed extract, tragacanth gum, starch, chemically modified starches and the like, semi-synthetic polymeric materials such as cellulose ethers (e.g. hydroxyethyl cellulose, methyl cellulose, carboxymethyl cellulose, hydroxy propylmethyl cellulose), polyvinylpyrrolidone, polyvinylalcohol, guar gum, hydroxypropyl guar gum, soluble starch, cationic celluloses, cationic guars and the like and synthetic polymeric materials such as carboxyvinyl polymers, polyvinylpyrrolidone, polyvinyl alcohol polyacrylic acid polymers, polymethacrylic acid polymers, polyvinyl acetate polymers, polyvinyl chloride polymers, polyvinylidene chloride polymers and the like. Inorganic thickeners may also be used such as aluminium silicates, such as, for example, bentonites, or a mixture of polyethylene glycol and polyethylene glycol stearate or distearate. Naturally occurring polymers or biopolymers and their use are further described in European Application No. 522624, to Dunphy et al. Additional examples of naturally occurring polymers or biopolymers can be found in the Cosmetic Bench Reference, pp. 1.40–1.42, herein incorporated by reference.

Also useful herein are hydrophilic gelling agents such as the acrylic acid/ethyl acrylate copolymers and the carboxyvinyl polymers sold by the B.F. Goodrich Company under the trademark of Carbopol Registered TM resins. These resins consist essentially of a colloidally water-soluble polyalkenyl polyether crosslinked polymer of acrylic acid crosslinked with from 0.75% to 2.00% of a crosslinking agent such as polyallyl sucrose or polyallyl pentaerythritol. Examples include Carbopol 934, Carbopol 940, Carbopol 950, Carbopol 980, Carbopol 951 and Carbopol 981. Carbopol 934 is a water-soluble polymer of acrylic acid crosslinked with about 1% of a polyallyl ether of sucrose having an average of about 5.8 allyl groups for each sucrose molecule. Also suitable for use herein are carbomers sold under the Trade Name "Carbopol Ultrez 10, Carbopol ETD2020, Carbopol 1382, Carbopol 1342 and Pemulen TR-1 (CTFA Designation: Acrylates/10–30 Alkyl Acrylate Crosspolymer). Combination of the above polymers are also useful herein. Other gelling agents suitable for use herein include oleogels such as trihydroxystearin.

Hydrophobically modified celluloses are also suitable for use herein. These celluloses are described in detail in U.S. Pat. Nos. 4,228,277 and 5,104,646, both of which are herein incorporated by reference in their entirety.

Additional examples of suitable gelling agents or gellants can be found in the Cosmetic Bench Reference, p. 1.27, herein incorporated by reference.

Without being limited by theory, the solidifying agent in combination with the emollient is believed to act as an occlusive on the skin by forming continuous or discontinuous bi-layer or multi-layer films on the skin. The term "occlusive," as used herein, means a preventing or obstructing something, in this case, preventing the removal of moisture (via evaporation) and the vitamin $B_3$ compound (via film binding) from the surface of the skin.

Color

Certain embodiments of the present invention, preferably lipsticks or lip paints, can contain from 1% to about 90%, preferably from about 1% to about 35%, more preferably from about 1% to about 20% and most preferably from about 5% to about 15%, of color, on an anhydrous pigment weight basis. These are usually aluminum, barium or calcium salts or lakes. Preferably, dyes are present at from about 0.1% to about 4% and pearls from 0% to about 20%.

Pigments are typically dispersed in emollients for the good dispersion of the pigments when incorporated into the lip compositions, thus providing an even distribution of color.

Colors/pigments suitable for use herein are all inorganic and organic colors/pigments suitable for use in lipstick compositions.

Lakes are either a pigment that is extended or reduced with a solid diluent or an organic pigment that is prepared by the precipitation of a water-soluble dye on an adsorptive surface, which usually is aluminum hydrate. There is uncertainty in some instances as to whether the soluble dye precipitates on the surface of the aluminum hydrate to yield a dyed inorganic pigment or whether it merely precipitates in the presence of the substrate. A lake also forms from precipitation of an insoluble salt from an acid or basic dye. Calcium and barium lakes are also used herein.

Lakes suitable for use in the present invention include Red 3 Aluminum Lake, Red 21 Aluminum Lake, Red 27 Aluminum Lake, Red 28 Aluminum Lake, Red 33 Aluminum Lake, Yellow 5 Aluminum Lake, Yellow 6 Aluminum Lake, Yellow 10 Aluminum Lake, Orange 5 Aluminum Lake and Blue 1 Aluminum Lake, Red 6 Barium Lake, Red 7 Calcium Lake.

Other colors and pigments can also be included in the lipsticks, such as dyes and pearls, titanium oxides, Red 6, Red 21, Brown, Russet and Sienna dyes, chalk, talc, zinc oxides, iron oxides and titanated micas.

Dispersants may also be used in conjunction with the colors and pigments of the present invention. Examples of suitable dispersants include, but are not limited to, those described in U.S. Pat. No. 5,688,493, herein incorporated by reference in its entirety.

Dermatologically Acceptable Anhydrous Carrier

The composition of the present invention may further comprise a dermatologically acceptable vehicle or carrier, in addition to the emollient component described herein before. Such a carrier should be compatible with the skin, the nails, the mucous membranes, tissues and the hair and includes any conventionally used cosmetic or dermatological carrier which meets these requirements. Such a carrier should also be compatible with the crystalline vitamin $B_3$ compound, in that it should not interact with or substantially dissolve the crystalline vitamin $B_3$ compound. The crystalline vitamin $B_3$ compound is preferably dispersed in the emollient component of the composition. The emollient can be part of the carrier system. Suitable carriers other than the emollients described herein before include, but are not limited to, oil-in-water emulsions, water-in-oil emulsions, ointments, lipsticks, foundations, mascaras, powders, suspensions, creams, lotions, gels, foams, mousses and the like. These carriers facilitate topical application and, in some cases, provide additional therapeutic effects, e.g., by moisturizing of the affected skin areas. Dermatologically acceptable carriers can be readily selected by one of ordinary skill in the art. Preferably, the carrier is substantially anhydrous. In this context, "substantially anhydrous" means that the carrier provides the composition with less than 20%, preferably less than 5%, more preferably less than 1%, most preferably 0%, by weight of free or unbound water by weight of the composition.

Substantially Free of Polar Solvents

The present invention is, preferably, substantially free of polar solvents. In general, "polar solvents" refers to those solvents that contain hydroxyl and/or carbonyl groups and also have high dielectric constants and strong polarity. In general, the phrase "substantially free" means the level of such polar solvents or polar solvent mixtures is preferably less than about 0.5%, more preferably less than 0.1% and is most preferably 0%. Without being limited by theory, such polar solvents tend to dissolve or otherwise interact with the crystalline structure of the vitamin $B_3$ compounds. Examples of such polar solvents include, but are not limited to, water; alcohols, such as ethanol, propyl alcohol, isopropyl alcohol, hexanol, and benzyl alcohol; polyols, such as propylene glycol, polypropylene glycol, butylene glycol, hexyleneglycol, maltitol, sorbitol, and glycerine; panthenol dissolved in glycerine; and mixtures thereof.

Other Additives

Other optional ingredients which can be present in the cosmetic compositions of the present invention include flavor oils, fat soluble vitamins such as vitamin A and E, esters of vitamin A (e.g., acetate, propionate, or palmitate) and of vitamin E (e.g., acetate or sorbate), sunscreens such as octyl methoxycinnamate, butyl methoxydibenzoylmethane, titanium dioxide and zinc oxide, germicides such as triclosan, anti-inflammatory agents such as hydrocortisone, lipid materials such as ceramides and liposomes and skin care actives. The cosmetic compositions can comprise ingredients conventionally employed in cosmetic compositions such as mascara, foundation or lipcare products. This includes skin care active ingredients such as pharmaceutically active ingredients.

Skin care actives ingredients in both water soluble and water insoluble forms can be added to the cosmetic compositions of the present invention. These include, but are not limited to vitamin C and its derivatives (e.g., ascorbyl palmitate, ascorbyl phosphate and its salts such as magnesium or sodium), vitamin D, panthenol, chalcones, flavanones, retinoic acid, titanium dioxide, iron oxides, zinc oxide, beta-glycyerhetic acid; chamomile oil; ginko biloba extract; pyroglutamic acid, salts or esters; sodium hyaluronate; 2-hydroxyoctanoic acid; sulfur; salicylic acid; carboxymethyl cysteine, and mixtures thereof.

These additives, both fat soluble and water soluble, will normally be present in amounts of less than about 10% by weight, and generally in the range of about 0.01% to about 5%, preferably from about 0.01% to about 3%, most preferably from about 0.1% to about 1%, by weight.

Organic binders such as stearic acid, paraffin, butyl acetate, copolymer of ethylene and vinyl acetate, methacrylic acid butyl ester, dibutyl phthalate, polyester and mixtures thereof can also be used in the present invention.

Flavor oils such as peppermint oil, orange oil, citrus oil, wintergreen oil can be used along with an alcohol or glycerine. Flavor oils are usually mixed in a solvent such as ethanol to dilute the flavor. The flavor oils useful herein can be derived from natural sources or be synthetically prepared. Generally flavor oils are mixtures of ketones, alcohols, fatty acids, esters and terpenes. The term "flavor oil" is generally recognized in the art to be a liquid which is derived from botanical sources, i.e. leaves, bark, or skin of fruits or vegetables, and which are usually insoluble in water. The level of flavor oil used can range from 0% to about 5%, preferably from 0% to about 1%.

Additional moisturizers may also be included into the present compositions. Preferred moisturizers include pyrrolidone carboxylic acid, sodium lactate or lactic acid, urea, guanidine, glyceric acid and its salts (e.g., calcium salt), petrolatum, collagen, α-hydroxy propylglyceryl ether, α-hydroxy acids (e.g., ethylglycolic acid, leucic acid, mandelic acid, glycolic acid), glucosamines, and elastin fibers, D-panthenol, allantoin and hyaluronic acid and chondroitin sulfate. Examples of suitable moisturizers can be found in Cosmetic Bench Reference, p. 1.30–1.32 (1996), herein incorporated by reference.

Surfactants can also be added to the compositions of the present invention. Suitable surfactants are those capable of forming association structures in contact with a polar solvent. Examples of such surfactants can be found in U.S. Pat. No. 5,843,407 to El-Nokaly, herein incorporated by reference. When used, the surfactants are preferably present at concentration of from about 0.1% to about 30%, more preferably 1% to about 15%, most preferably from about 1% to about 5% by weight of the composition.

Also useful herein are emulsifiers commonly known as coupling agents. When used, the overall concentration of the emulsifier can be from about 0.1% to about 30%, preferably from 1% to about 15% and most preferably from about 1% to about 15%, most preferably from about 1% to about 5% by weight of the composition. Examples of suitable emulsifiers can be found in U.S. Pat. No. 5,085,856 to Dunphy et al.; Japanese Patent Publication Sho 61-83110; European Patent Application EP 522624 to Dunphy et al.; U.S. Pat. No. 5,688,831 to El-Nokaly et al.; and examples of other suitable emulsifiers can be found in Cosmetic Bench Reference, pp. 1.22, 1.24–1.26 (1996), all of which are herein incorporated by reference in their entirety.

Mixtures of the above surfactants and emulsifiers can also be used.

A preferred optional component is ethyl cellulose (Ethocel). Ethyl cellulose generally is preferred for use at levels of about 5% and more preferably 1%.

Another preferred optional component is silica. Silica is generally preferred for use at levels of from about 1% and about 5%.

Hypoallergenic compositions can be made from the liquid crystal, wax, oil and colors herein. These compositions should not contain fragrances, flavor oils, lanolin, sunscreens, particularly PABA, or other sensitizers or potential sensitizers and irritants.

The compositions of the present invention can also be made into long lasting or non-transferable cosmetic compositions. Detailed discussions of such lipsticks are found in Japanese Patent Publication Hei No. 6-199630 and European Patent Application 748622, both of which are herein incorporated by reference in their entirety.

Additional optional materials that can be incorporated in the compositions of the present invention can be found in PCT application WO 97/39733, to Oblong et al.

Methods of Use

The cosmetic compositions of the present invention are ideally suited for use in treating the skin and lips, especially in the form of a lipstick or lip balm for applying to the lips a permanent or semi-permanent color, ideally with a gloss or luster finish. The cosmetic compositions can also be used in treating the skin and/or lips with a skin care agent for protection against exposure to adverse weather, including the wind and the rain, dry and/or hot environments, environmental pollutants (e.g., ozone, smoke, and the like), or exposure to excessive doses of sunlight. The compositions are also useful in providing sun protection, moisturizing and/or conditioning for the hair and skin, improved skin feel, regulating skin texture, reducing fine lines and wrinkles, reducing oily shine on hair or skin, skin lightening and reducing skin or hair odor.

The cosmetic compositions can, accordingly, be applied to the skin and/or lips in the traditional manner using a convenient holder or applicator to provide a decorative and/or protective film thereto.

Methods of Determining Solubility of Vitamin $B_3$ Compounds in Emollients

The solubility of the vitamin $B_3$ compound in the various non-polar emollients of the present invention can be determined as follows:

I. Preparation of Samples for Analysis
  1) the emollient is placed in pre-weighted vial and then saturated with a vitamin $B_3$ compound;
  2) the vial is shaken and allowed to sit in a bath at 30° C. for 1 hour. A small stir bar is used to agitate the contents of the vial. If no precipitation occurs in the vial, then more niacinamide is added. This was repeated until precipitation occurred. The sample is left in the bath for an additional 48 hours to insure saturation;
  3) the saturated emollient is drawn into a syringe;
  4) A 0.45 micron filter (Gelman Acrodisc) is fitted on the end the syringe and the emollient is filtered through into separate pre-weighted vial for analysis;
  5) The emollient is analyzed using HPLC to determine the amount of niacinamide therein.

II. Analysis

Approximately 0.25 g of the sample is weighed (sample weight) into a 15 mL plastic screw-cap centrifuge tube. The sample is mixed with approximately 3 mL of 50/50 v/v methanol/chloroform and homogenized by vortex mixing. About 7 mL of water is then added to extract the vitamin $B_3$ compound from the methanol/chloroform phase. Each sample is mixed by shaking 50 times in a back and forth motion to facilitate transfer of the niacinamide from the methanol/chloroform to the water phase. This mixing creates an emulsion at the interface of the two phases. The emulsion can be dissipated by letting the sample stand for several hours or by brief centrifugation (15 seconds) at high speed. Once the two phases have completely separated, a pipette is used to carefully transfer the aqueous phase into a separate, pre-weighted vial. The weight of the aqueous phase is noted (aqueous phase weight). An aliquot of the aqueous phase is transferred to an analysis container and analyzed for niacinamide by HPLC (Waters 2690 Separations Module coupled with a Waters 996 PDA detector, both supplied by Waters Corporations).

III. Calculations

The percent vitamin $B_3$ compound is determined by taking the vitamin $B_3$ compound concentration measured by HPLC and multiplying by the dilution factor. The dilution factor is the aqueous phase weight divided by the sample weight.

EXAMPLES

The cosmetic formulations illustrated in Examples I–X illustrate specific embodiments of the cosmetic compositions of the present invention, but are not intended to be limiting thereof. Other modifications can be undertaken by the skilled artisan without departing from the spirit and scope of this invention. These exemplified embodiments of the cosmetic compositions of the present invention improve the skin penetration of the vitamin $B_3$ compound while also improving skin feel of the crystalline vitamin $B_3$ compound.

All exemplified compositions can be prepared by conventional formulation and mixing techniques. Such formulation and mixing techniques are described in detail in *Harry's Cosmeticology*, pp. 119–141 and 314–354 (J. B. Wilkinson and R. J. Moore $7^{th}$ ed 1982), and *Cosmetics: Science and Technology*, pp. 1–104 and 307–422 (M. S. Balsam and E. Sagarin $2^{nd}$ ed 1972), both of which are herein incorporated by reference in their entirety. Component amounts are listed as weight percents and exclude minor materials such as diluents, filler, and so forth. The listed formulations, therefore, comprise the listed components and any minor materials associated with such components.

Example I-Lipstick Composition

| Ingredient | Amount (weight percent) |
| --- | --- |
| Ozokerite Wax | 5.00 |
| Candelilla Wax | 3.00 |
| Carnauba Wax | 2.00 |
| Cetyl Alcohol | 2.00 |
| Cetyl Lactate | 2.00 |
| Ascorbyl Palmitate | 0.50 |
| Propylparaben | 0.10 |
| Vitamin E Acetate | 0.05 |
| Isopropyl Isostearate | 13.97 |
| Octyl Hydroxystearate | 5.20 |
| Paraffin Wax | 2.50 |
| Tocopherol nicotinate (23%) + castor oil (77%) dispersion (ball milled)[1] | 21.74 |
| Acetylated Lanolin | 6.33 |
| Mica SVA | 10.00 |
| Pigment Slurry (30% Pigment/70% Castor oil) | 25.61 |

[1]The crystalline tocopherol nicotinate is combined with castor oil and ball milled to an average crystalline particle size of from about 0.01 μm to about 200 μm.

The milled tocopherol nicotinate/castor oil mixture along with the remaining ingredients of the above formulation are added to a vessel equipped with a heat source and heat the ingredients to a temperature of about 90° C. to form a melt. The melt is mixed until homogeneous. The mixture is deaerated by vacuum and poured into the appropriate mold. The mixture is cooled to ambient temperature and incorporated into the appropriate package.

The lipstick is applied to the lips to provide color, moisturization and improved lip feel.

Example II-Lipstick Composition

| Ingredient | Amount (weight percent) |
| --- | --- |
| Ozokerite Wax | 5.00 |
| Candelilla Wax | 3.00 |
| Carnauba Wax | 2.00 |
| Cetyl Alcohol | 2.00 |
| Cetyl Lactate | 2.00 |
| Ascorbyl Palmitate | 0.50 |
| Propylparaben | 0.10 |
| Vitamin E Acetate | 0.05 |
| Isopropyl Isostearate | 15.00 |
| Octyl Hydroxystearate | 10.00 |
| Paraffin Wax | 2.50 |
| niacinamide[1] | 2.50 |
| Castor oil | 13.41 |
| Acetylated Lanolin | 6.33 |
| Mica SVA | 10.00 |
| Pigment Slurry (30% Pigment/70% Castor oil) | 25.61 |

[1]The crystalline niacinamide is milled with castor oil to an average crystalline particle size of from about 0.01 μm to about 200 μm.

The milled niacinamide, together with the remaining ingredients of the above formulation, are added to a vessel equipped with a heat source and heat the ingredients to a temperature of about 90° C. to form a melt. The melt is mixed until homogeneous. The mixture is deaerated by vacuum and poured into the appropriate mold. The mixture is cooled to ambient temperature and incorporated into the appropriate package.

The lipstick is applied to the lips to provide color, moisturization and improved lip feel.

Example III-Lipstick Composition

| Ingredient | Amount (weight percent) |
| --- | --- |
| Glycerine | 0.300 |
| Lecithin | 2.00 |
| Niacinamide[1] | 5.00 |
| Octyl Palmitate | 11.24 |
| Isopropyl Palmitate | 4.80 |
| Bentone 38 | 1.00 |
| Propylene Carbonate | 0.33 |
| Cetyl Recinolate | 1.00 |
| Diisopropyl Dimearate | 29.88 |
| Lanolin Oil | 11.60 |
| Ozokerite | 6.75 |
| Candelilla | 5.25 |
| Be Square 175 | 2.00 |
| PG-3 Diisostearate | 2.00 |
| Vitamin "E" Acetate | 0.05 |
| Propylparaben | 0.15 |
| Methylparaben | 0.15 |
| Benzoic Acid | 0.10 |
| Mica cf | 7.00 |
| Pigments | 9.00 |
| Stainers | 0.40 |

[1]The crystalline niacinamide is milled with an emollient (e.g., diisopropyl dimearate) to an average crystalline particle size of from about 0.01 μm to about 200 μm.

In a suitable vessel, the glycerine, lecithin and milled niacinamide are mixed in an appropriate vessel until a liquid crystal phase is formed.

Separately, the remaining ingredients of the above formulation are added to a vessel equipped with a heat source and heated to a temperature of about 90° C. to form a melt. The melt is mixed until homogeneous. The above liquid crystal phase mixture is added to the melt and mixed until homogeneous. The mixture is deaerated by vacuum and poured into the appropriate mold. The mixture is cooled to ambient temperature and incorporated into the appropriate package.

The lipstick is applied to the lips to provide color, moisturization and improved lip feel.

Example IV-Antiperspirant Gel Stick

| Ingredient | Amount (weight percent) |
|---|---|
| Tocopherol nicotinate[1] | 4 |
| N-Lauroyl-L-glutamic-acid-di-n-butyl amide[2] | 4 |
| 12-hydroxystearic acid | 2 |
| Light mineral oil[3] | 23 |
| Diisopropyl Sebacate[4] | 39 |
| Aluminum Zirconium | 25 |
| Talc | 3 |

[1]The crystalline tocopherol nicotinate is milled with mineral oil to an average crystalline particle size of from about 0.01 μm to about 200 μm.
[2]GP-1 supplied by Ajinomoto, Inc.
[3]Benol White Mineral Oil supplied by Witco Chemical Corp.
[4]Schercemol DIS supplied by Scher Cherfficals Inc.

The gelling agent, milled tocopherol nicotinate and the liquid base material are combined into a vessel equipped with a heat source. The mixture is heated to a temperature between about 80° C. and about 130° C. with stirring, until the mixture forms a homogeneous, molten solution. Preferably, the homogeneous, molten solution is allowed to cool to a mixing temperature; typically between about 65° C. and 110° C. Next, the antiperspirant active and other ingredients are added to the melt, such as fragrances and colors, into the homogeneous, molten solution in the above vessel with stirring. The mixture is allowed to cool until it begins to thicken and poured into containers allowing them to cool to ambient temperature. (Although not preferred, the antiperspirant active may alternatively be added along with the gelling agent and the liquid base material in the first step.)

An antiperspirant composition, comprised as above, is applied to the underarm area of a human subject, and has improved skin feel.

Example V-Solid Antiperspirant Stick

| Ingredient | Amount (weight percent) |
|---|---|
| Niacinamide[1] | 3.0 |
| Stearyl Alcohol | 10.0 |
| Hydrogenated Castor Oil-mp 86 degrees C. | 9.0 |
| Aluminum Chlorohydroxide | 40.0 |
| Isopar "V"[2] | 37.0 |
| Fragrance | 1.0 |
| | 100.0 |

[1]The crystalline niacinamide is milled to an average crystalline particle size of from about 0.01 μm to about 200 μm
[2]Isopar "V" Avg. Mol. Wt. 197 B.P. Range, 255–301 degrees Celsius.

In vessel containing a heat source, the isoparaffin liquids, the water-insoluble liquid emollients, the surface active agent, and the water-insoluble waxes are heated to a temperature sufficient to form a solution of these materials. Next, the aluminum chlorohydroxide is added with gentle agitation, followed by the milled niacinamide and remaining ingredients. The solution is mixed until a homogenous suspension is formed. The suspension is cooled to a temperature above the solidification point and is then poured into suitable containers.

An antiperspirant composition, comprised as above, is applied to the underarm area of a human subject, and has improved skin feel.

Example VI-Solid Antiperspirant Stick

| Ingredient | Amount (weight percent) |
|---|---|
| Niacinamide[1] | 1 |
| Stearic Acid | 10.0 |
| Hydrogenated Castor Oil-mp 86 degrees C. | 5.5 |
| Zirconium Chlorohydroxide | 25.0 |
| Talc | 10.0 |
| Isopar "M"[2] | 42.5 |
| Diisopropyl Adipate | 5.0 |
| Fragrance | 1.0 |
| | 100.0 |

[1]The crystalline niacinamide is milled with castor oil to an average crystalline particle size of from about 0.01 μm to about 200 μm.
[2]Isopar "M", Avg. Mol. Wt. 191 B.P. Range, 207–260 degrees Celsius.

In vessel containing a heat source, the isoparaffin liquids, the water-insoluble liquid emollients, the surface active agent, and the water-insoluble waxes are heated to a temperature sufficient to form a solution of these materials. Next, the aluminum chlorohydroxide is added with gentle agitation, followed by the milled niacinamide and remaining ingredients. The solution is mixed until a homogenous suspension is formed. The suspension is cooled to a temperature above the solidification point and is then poured into suitable containers.

An antiperspirant composition, comprised as above, is applied to the underarm area of a human subject, and has improved skin feel.

Example VII-Antiperspirant Cream

| Ingredient | Amount (weight percent) |
|---|---|
| [1]Niacinamide | 3.0 |
| cyclomethicone (D5) | 40.5 |
| dimethicone (350 cs) | 4.0 |
| Cab-O-Sil HS-5[2] | 4.0 |
| Microthene FN510[3] | 6.0 |
| Natrosol[4] | 2.0 |
| iso-eicosane[5] | 13.0 |
| Reach AZ[6] | 26.7 |
| fragrance | 0.8 |

[1]The crystalline niacinamide is milled with dimethicone (350 cs) to a particle size of from about 0.01 μm to about 200 μm.
[2]Colloidal silica thickening material, sold by Cabot Corporation.
[3]Low density polyethylene powder, sold by U.S.I. Chemicals.
[4]Hydroxyethylcellulose, sold by Hercules, Inc.
[5]2,2,4,4,6,6,8,8-dimethyl-10-methylundecane, obtained from Permethyl Corporation, Frazier, PA.
[6]Zirconium-aluminum-glycine hydroxychloride complex, particulate antiperspirant active material, sold by Reheis Chemical Company.

The cyclomethicone, iso-eicosane and perfume are added to a stainless steel mixing vessel. The Cab—O—Sil is then added, followed by the Microthene and Natrosol and, finally, the antiperspirant active and milled niacinamide. The composition is thoroughly stirred after addition of each particulate material.

The composition is then milled, using a Black & Decker Die Grinder (Model 4420, type 4) with a 6.35 cm diameter Cowles dispersing blade at approximately 6,000 rpm, for approximately 5 minutes until having the desired consistency.

An antiperspirant cream formulation, comprised as above, is applied to the underarm area of a human subject, and has improved skin feel.

Example VIII-Waterproof Mascara

| Ingredient | Amount (weight percent) |
| --- | --- |
| Petroleum Distillate ((IBP 345) | 49.570 |
| Glycerol Ester of Tall Oil Rosin | 10.000 |
| Bentone 38 CG or Type | 5.890 |
| Color (Black 34-3068 or Type) | 5.000 |
| Alkylated PVP (220 Type) | 5.000 |
| Trihydroxystearin (R Type) | 5.000 |
| Magnesium Carbonate 309 | 5.000 |
| [1]Tocopherol nicotinate | 5.000 |
| Kaolin 2747 | 2.000 |
| Carnauba Wax, NF | 2.000 |
| Propylene Carbonate | 1.940 |
| Polyethylene AC-617A | 1.000 |
| Phenoxyethanol | 0.800 |
| Color (Yellow 34-3170 or Type) | 1.600 |
| Propylparaben, NF | 0.100 |
| Tenox BHA | 0.100 |
| Total | 100.000 |

[1]The crystalline tocopherol nicotinate is milled with the petroleum distillate ((IBP 345) to an average crystalline particle size of from about 0.01 $\mu$m to about 200 $\mu$m.

The milled tocopherol nicotinate and the above ingredients except colorants and gellants/fillers are added into stainless steel mixing vessel equipped with a heating source. The ingredients are heated to a temperature of about 90° C. and mixed using a propeller blade. Once the temperature reaches about 90° C., the ingredients are mixed using a dispersator blade at approximately 3500 rpm. The pigments are then slowly added during the mixing with the dispersator. Similarly, the gellants/fillers are added with mixing. The mixing is continued with the dispersator until the mixture is homogeneous. The mixture is then forced cooled while mixing with the dispersator at 3500 rpm. At about 40° C., mixing is discontinued and the mixture is transferred into an appropriate storage container.

The mascara composition is applied to the lashes and/or eyebrows to provide softening, moisturization and improved feel.

Example IX-Mascara

| Ingredient | Amount (weight percent) |
| --- | --- |
| Petroleum Distiliate (IBP 345) | 51.570 |
| Glycerol Ester of Tall Oil Rosin | 10.000 |
| Bentone 38 CG or Type | 5.890 |
| Magnesium Carbonate 309 | 5.000 |
| Alkylated PVP (220 Type) | 5.000 |
| Trihydroxystearin (R Type) | 5.000 |
| Talc 2755 | 4.790 |
| Niacinamide | 3.000 |
| Kaolin 2747 | 2.000 |
| Carnauba Wax, NF | 2.000 |
| Propylene Carbonate | 1.940 |
| Polyethylene AC-617A | 1.000 |
| Phenoxyethanol | 0.800 |
| Propylparaben, NF | 0.100 |
| Tenox BHA | 0.100 |
| Color (Blue 3403516 or Type) | 1.810 |
| Total | 100.000 |

The composition is prepared and used as in Example VIII.

Example X-Mascara

| Ingredient | Amount (weight percent) |
| --- | --- |
| Petroleum Distillate (IBP 345) | 50.670 |
| Glycerol Ester of Tall Oil Rosin | 10.000 |
| Bentone 38 CG or Type | 5.890 |
| Magnesium Carbonate 309 | 5.000 |
| Trihydroxystsearin (R Type) | 5.000 |
| Carnauba Wax, NF | 2.000 |
| Niacinamide | 10.000 |
| Kaolin 2747 | 2.000 |
| Propylene Carbonate | 1.940 |
| Polyethylene AC-617A | 1.000 |
| Phenoxyethanol | 0.800 |
| Color | 5.500 |
| Tenox BHA | 0.100 |
| Propylparaben, NF | 0.100 |
| Total | 100.000 |

The composition is prepared and used as in Example VIII.

Example XI-Lipstick

| INGREDIENT | WT. %. |
| --- | --- |
| Polybutene | 4.536 |
| Lanolin Oil | 18.342 |
| Octoxyglyceryl Behenate | 18.342 |
| Stearyl heptanoate | 8.856 |
| Jojoba oil | 8.856 |
| castor oil | 21.78 |
| Butylated hydroxytoluene | 0.054 |
| Butylated hydroxyanisole | 0.054 |
| Microcrystalline Wax | 6.84 |
| Polyethylene 500 | 6.84 |
| Niacinamide | 4.5 |
| (Amphiphlic lipid phase) | |
| Lecithin | 0.475 |
| Cholesterol | 0.475 |
| dicetyl phosphate | 0.05 |

In a suitable vessel, neat, chemically synthesized crystalline niacinamide is dissolved using an appropriate solvent. The niacinamide is then recrystallized by the single solvent method. Next, the recrystallized niacinamide is combined with the castor oil and milled to the appropriate particle size.

Separately, the milled niacinamide/castor oil mixture, polybutene, lanolin oil, octoxyglyceryl behenate, stearyl heptanoate, jojoba oil, butylated hydroxytoluene, butylated hydroxyanisole, microcrystalline wax, polyethylene 500 are added to a vessel equipped with a heat source and heated to a temperature of from about 100–110° C. to form a melt. The melt is mixed until homogeneous. The lecithin, cholesterol and dicetyl phosphate are mixed separately under nitrogen and at a temperature of about 110° C. The lecithin containing mixture is then added to the niacinamide containing mixture and mixed until uniform. The mixture is deaerated by vacuum and poured into the appropriate mold. The mixture is cooled to ambient temperature and incorporated into the appropriate package.

The lipstick is applied to the lips to provide color, moisturization and improved lip feel.

Example XII-Lip Balm

| INGREDIENT | WT. %. |
| --- | --- |
| SEFA Cottonate | 84.000 |
| Niacinamide | 5.000 |
| Candelilla Wax | 3.000 |
| Ozokerite Wax | 1.000 |
| Microcrystalline Wax | 1.500 |
| Beeswax | 5.300 |
| BHT | 0.050 |
| Ethylene Brassylate | 0.050 |
| Propylparaben | 0.100 |
| | 100.000 |

In a suitable vessel, the niacinamide is mixed with SEFA Cottonate and milled to the appropriate particle size.

The SEFA Cottonate/niacinamide mixture along with the remaining ingredients are added to a vessel equipped with a heat source and heated to a temperature of from about 80–90° C. to form a melt. The melt is mixed until homogeneous. The mixture is deaerated by vacuum and poured into the appropriate mold. The mixture is cooled to ambient temperature and incorporated into the appropriate package.

The lipstick is applied to the lips to provide moisturization and improved lip feel.

Example XIII-Long-LastingCosmetic

| INGREDIENT | WT. %. |
| --- | --- |

A. An admixture (Part A) is prepared by combining in a suitable vessel the following ingredients:

| MQ Resin[1] | 43.7 |
| --- | --- |
| PM99A[2] | 56.3 |

[1]Trimethylsiloxysilicate available from GE.
[2]Isododecane available from Presperse.
The admixture is mixed using conventional mixing techniques until the MQ Resin is dissolved.
Processing:

B. An admixture (Part B) is prepared by combining in a suitable vessel the following ingredients:

| SE30 Silicone Gum[1] | 50.0 |
| --- | --- |
| PM99A | 50.0 |

[1]Available from GE.
The admixture is mixed using conventional mixing techniques until the SE30 Silicone Gum is dissolved.
C. A lipstick containing Part A and Part B is prepared by combining the following ingredients:

| Tocopherol nicotinate | 1.00 |
| --- | --- |
| Part A | 47.00 |
| Part B | 24.91 |
| Pigment(s) | 10.00 |
| Propylparaben | 0.20 |
| PM99A | 1.89 |
| Bentone ISD[1] | 15.00 |

[1]10% bentone, 3% propylene glycol, 87% Isododecane available from Rheox

In a suitable vessel, the admixture of Part A along with the pigments, propylparaben, crystalline tocopherol nicotinate and PM99A are combined and mixed using a Ross homogenizer at about 4,000 rpms. for about 10 minutes or until the mixture is uniform (taking care not to ignite the PM99A). The Bentone ISD added to the mixture with mixing at about 4,000 rpms. until the mixture is uniform. The admixture of Part B is added to the mixture and mixed initially at high shear, preferably 1600 rpms., to facilitate dispersion using a IKA mixer. Once sufficient dispersion is achieved, the mixer speed is reduced, preferably to about 1,000 rpms., and the mixture is allowed to mix until uniform. The mixture is then poured into a suitable container and tightly capped for storage, preferably at room temperature.

The long lasting cosmetic composition is applied to the skin to provide color, moisturization and improved skin feel.

What is claimed is:

1. A lipstick composition containing crystalline vitamin $B_3$ compounds, and which provides improved skin feel, said composition comprising:

a) from about 0.01% to about 50%, by weight, of crystalline vitamin $B_3$ compound particles present in said composition, having an average particle size of from about 0.01 μm to about 200 μm;

b) from about 1% to about 90%, by weight, of an emollient component; and c) from about 1% to about 90%, by weight, of a solidifying agent, wherein the solubility (30°) of the vitamin $B_3$ compound in the emollient is less than about 1.5%.

2. A lipstick composition according to claim 1, wherein the average particle size of the vitamin $B_3$ compound is from about 0.01 μm to about 100 μm.

3. A lipstick composition according to claim 1, wherein at least 60% of the vitamin $B_3$ compound has a particle size of less than 30 μm.

4. A lipstick composition according to claim 1, wherein said vitamin $B_3$ compound is selected from the group consisting of niacinamide, derivatives of niacinamide, non-vasodilating esters of nicotinic acid, and combinations thereof.

5. A lipstick composition according to claim 4, wherein said vitamin $B_3$ compound is selected from the group consisting of niacinamide, tocopherol nicotinate, and combinations thereof.

6. A lipstick composition according to claim 5, wherein said vitamin $B_3$ compound is niacinamide.

7. A lipstick composition according to claim 1, wherein said vitamin $B_3$ compound is substantially free of salts of the vitamin $B_3$ compound.

8. A lipstick composition according to claim 1, wherein said vitamin $B_3$ compound is substantially uncomplexed.

9. A lipstick composition according to claim 1, wherein said composition is substantially free of polar solvents.

10. A lipstick composition according to claim 1, wherein said emollient component comprises from about 10% to about 80% of the cosmetic composition.

11. A lipstick composition according to claim 10, wherein an oil comprises from about 5% to about 90% of the emollient component.

12. A lipstick composition according to claim 10, wherein said emollient is a non-polar emollient.

13. A lipstick composition according to claim 11, wherein said oil is selected such that at least about 75% of the oil has solubility parameters which do not differ by more than from about 0.1 to about 1.

14. A lipstick composition according to claim 13, wherein said oil is selected such that at least about 99% of the oil has solubility parameters which do not differ by more than from about 0.1 to about 1.5.

15. A lipstick composition according to claim 1, further comprising from about 0.1% to about 35% of a color.

16. A lipstick composition according to claim 1 wherein the vitamin $B_3$ compound is dispersed in the emollient.

17. A method of improving the perceived skin feel of crystalline vitamin $B_3$ compounds by applying to the skin a safe and effective amount of the lipstick composition in claim 1.

18. A lipstick composition according to claim 1 wherein the composition comprises less than about 10%, by weight of the composition formed, of water.

19. A topical cosmetic composition providing improved skin feel of crystalline vitamin $B_3$ compounds, said composition comprising:
   a) from about 0.01% to about 50%, by weight, of crystalline vitamin $B_3$ compound particles present in said composition, having an average particle size of from about 0.01 μm to about 200 μm; and
   b) from about 1% to about 90%, by weight, of an emollient component, wherein the solubility (30°) of the vitamin $B_3$ compound in the emollient is less than about 1.5%.

20. The composition according to claim 19 wherein the vitamin $B_3$ compound is niacinamide.

21. The composition according to claim 19 wherein the vitamin $B_3$ compound is dispersed in the emollient.

22. The composition according to claim 19 wherein the average particle size of the vitamin $B_3$ compound is from about 0.01 μm to about 100 μm.

23. The composition according to claim 19 wherein the composition is substantially free of polar solvents.

24. The composition according to claim 19 wherein the vitamin $B_3$ compound is dispersed in the emollient.

* * * * *